United States Patent [19]

Mitz

[11] Patent Number: 5,116,389
[45] Date of Patent: May 26, 1992

[54] METHOD OF OBTAINING COLLAGEN HUMAN-SKIN FIBERS, FIBERS THUS PRODUCED, AND A COMPOUND CONTAINING THEM

[76] Inventor: Vladimir Mitz, 176, boulevard Saint-Germain, F 75006 Paris, France

[21] Appl. No.: 545,520

[22] Filed: Jun. 28, 1990

[30] Foreign Application Priority Data

Jan. 4, 1989 [FR] France ................... 8900056

[51] Int. Cl.$^5$ ........................... D06M 13/00
[52] U.S. Cl. ......................... 8/127.5; 8/94.11; 128/DIG. 8; 530/356
[58] Field of Search ................. 8/94.11, 127.5; 623/1, 623/2, 3; 530/356; 128/DIG. 8

[56] References Cited

U.S. PATENT DOCUMENTS 3,949,073  4/1976  Daniels et al. ............... 424/177

FOREIGN PATENT DOCUMENTS 0089145  9/1983  European Pat. Off.
0196197  10/1986  European Pat. Off.
2328786  5/1977  France

*Primary Examiner*—Prince Willis, Jr.
*Assistant Examiner*—John F McNally
*Attorney, Agent, or Firm*—Herbert Dubno; Andrew Wilford

[57] ABSTRACT

Human-skin collagen fibers are obtained from sterile pieces of human skin by first comminuting the sterile skin and then mixing the comminuted sterile skin with a sterile aqueous solution of an alkaline-metal or alkaline-earth salt to form a suspension. This suspension is then diluted with a promoter of fibrillogenesis taken from the group formed by acetylated glucosamine, n-acetyl neuraminic acid, and mixtures thereof and the pH of the suspension is set to a value between 4 and 6. The diluted suspension is then left to ripen while fibers grow in it. Collagen fibers are then separated from the suspension and are checked under a microscope for the presence of protein impurities. If any such fraction is then found the fibers are rinsed by agitation with an atoxic aqueous solution of a nonionic detergent, then the residual protein impurities are separated out to obtain an aqueous suspension of collagen fibers having no foreign matter, and finally the collagen fibers are rinsed in steriized water. The fibers thus obtained are implanted back into the patient from whom the skin was originally recovered.

13 Claims, No Drawings

METHOD OF OBTAINING COLLAGEN HUMAN-SKIN FIBERS, FIBERS THUS PRODUCED, AND A COMPOUND CONTAINING THEM

FIELD OF THE INVENTION

The invention relates to a method of obtaining human collagen fibers and of using these fibers for therapeutic treatments, namely in cosmetic surgery.

BACKGROUND OF THE INVENTION

It is well-known that collagen is a protein that is very abundant in man. It is found in most tissues and organs and in particular in the skin. Collagen constitutes organized structures and in particular fibers having a length of between one-tenth of a millimeter and several millimeters and a diameter of several hundreds of nanometers, these fibers having transverse striations about every 70 nanometers. These collagen fibers are formed by groups of tropocollagen fibrils, these fibrils forming the basic element constituting human collagenic material.

Several methods have been proposed which extract from animal tissue a collagenic fraction by means of an aqueous solution of an alkaline-metal or alkaline-earth salt (see in particular GOLDSTEIN, C. R. ACADEMIE DES SCIENCES DE PARIS, volume 268, pages 2446-2448 and the bibliography therein), but the collagen thus obtained is not in the form of organized fibers as are found in conjunctive tissue.

It is known in cosmetic surgery to correct skin depressions that are the result of acne, accidental injuries, or simple aging by injecting into these skin depressions a collagenic material. Up to the present the collagenic material that is injected is generally obtained from cattle. The injections are carried out by means of fine needles right at the region of the breaks in the skin. Unfortunately bovine collagen thus in place constitutes relative to the human organism into which it is injected a foreign body which is attacked by an enzyme, collagenase, that is secreted by fibroblasts of the subject under treatment. The result is that the added collagen implaced is reabsorbed in several months so that this type of treatment is not satisfactory. In order to avoid this disadvantage it would be necessary on one hand to be able to place in the skin breaks a collagen of the same type (that is type I and III) of human origin and it would be necessary on the other hand that this collagen be in the form of collagenic fibers in order to be able to reconstitute a skin matrix having the same characteristics as the collagenic matrix of the conjunctive tissue of the subject in the regions adjacent the treated region.

OBJECT OF THE INVENTION

It is therefore an object of the instant invention to overcome the above-disadvantages of the known process.

SUMMARY OF THE INVENTION

This object is attained in that it is proposed to recover a starting material from a human subject, to extract from it the collagen fibrils by separating all of the non-collagenic materials surrounding the tissue so as to purify the starting material, to reconstruct in vitro the collagen fibers starting from the fibrils thus obtained, and to use these fibers in suspension for intradermal injections. Furthermore according to a complimentary characteristic of the invention it is proposed to augment the tolerance of the patient under treatment relative to the collagenic fibers by using as a starting material pieces of skin of this patient under treatment. This technique has as far as tolerance is concerned the same advantage as autografting and in addition it avoids any risk relative to transmitting diseases by means of encapsulated viruses of the HIV (SIDA) or similar type.

According to the invention it has been confirmed that the collagen fibrils that can be obtained and isolated in the known manner are susceptible of reorganizing themselves in collagen fibrils identical to those that are found in human conjunctive tissue when in a diluted environment they are put in the presence of a fibrillogenesis promoter of slightly acid pH. According to the invention it has been discovered that the amount of collagen fibers that are reconstituted was sufficient to support a process that is usable in practice when one chooses as fibrillogenesis promoter acetylated glucosamine or neuraminic N-acetyl acid or mixtures thereof. One thus obtains suspensions of collagen fibers in an aqueous environment. In order to be able to use these suspensions in cosmetic surgery without being obligated to sterilize, for example, by irradiation, the compositions thus obtained, the recovery procedure is run sterile from the first to the last step, and this is perfectly sufficient due to the short conversion time that takes place between the moment when the injectable substance is obtained and when it is used on the patient, due to the autogenic character of the product.

The present invention thus has as its object a process of obtaining human-skin collagen fibers starting from collagen fibrils extracted in a known manner from sterilized pieces of human skin by mixing, after comminution, with a sterile aqueous solution of an alkaline-metal or alkaline-earth salt, characterized by the fact that in a first step the collagen fibers are reconstituted after dilution of the suspension of the fibrils by adding to said suspension a promoter of fibrillogenesis taken from the group formed by acetylated glucosamine, n-acetyl neuraminic acid, and mixtures thereof, the pH being set at a value between 4 and 6, and then letting it sit so the fibers can grow, and thereafter in a second step separating from the mother liquor the obtained collagen fibers and checking them under a microscope to verify that the collagen fibers are devoid of protein fractions that they had as a starting material, any insufficient separation resulting in to start with a rinsing of the fibers by agitation with an atoxic aqueous solution of a nonionic detergent followed by a separation out of the residual protein fractions to obtain an aqueous suspension of collagen fibers having no foreign matter, then at least one rinsing in sterilized water and finally in a third step the fibers are prepared for their eventual use.

In a preferred mode for carrying out the process according to the invention the extraction of the fibers is done by means of an aqueous solution of a magnesium salt at a basic pH below 8. The fibers are extracted in several consecutive substeps, the first substep of extraction producing a solid residue that is taken up in a following extraction substep, the molar concentration of magnesium salt of the extraction solution increasing progressively from 0.1M to 1M in passing from the first to the last substep.

In a first step of the process according to the invention the suspension of fibrils is subjected to the action of a fibrillogenesis promoter. One uses preferably this promoter at a concentration of between 0.005M and 0.05M in the suspension after dilution. First of all the temperature is raised to a level between 30° C. and 50° C., preferably about 37° C., for time less than 2 hours after which the suspension is left to sit for a time of between 10 hours and 50 hours at a temperature between 0° C. and 10° C., preferably about 4° C. In the initial step, when the temperature is high, the formation of fibers is started whereas in the second phase, as it sits, the fibers have time to develop. The result is that the times indicated above are not critical and that they simply correspond to values sufficient to obtain a particularly satisfying development of the collagen fibers. It should be noted that in order to ensure a proper action of the fibrillogenesis promoter, the fibril suspension as obtained in the extraction step should be diluted. Preferably this suspension is diluted from ten to thirty times by addition of sterile water.

It is also possible to separate this mother liquor of the reconstituted fibers by decantation, by removal of the floating phase, the remaining phase being recovered by straining so that the filtrate contains the collagen fibers.

The suspension of collagenic fibers is checked by a microscope, normally an electron microscope. If one determines that proteins are stuck to the collagen fibers, the fibers are rinsed with a sorbitan solution (commercial product under the tradename called "TWEEN 20"). The rinse solution has a concentration by weight of sorbitan advantageously comprised between 0.05% and 0.4% and preferably around 0.2%.

The present invention also has as its object the collagen fibers obtained according to the process described above.

The invention also has as its object an injectable compound utilized for treating the human body, characterized in that it is constituted as a suspension in an aqueous phase of collagen fibers as described above at a concentration between 1% and 15% by volume, preferably between 5% and 10% by volume.

The aqueous phase of the compound according to the invention is advantageously a sodium buffer having a pH of between 7 and 7.5. This buffer can be for example a "PBS" buffer containing 0.1M of monosodium phosphate, 0.1M of disodium phosphate, and 0.1M of sodium chloride.

The composition of the invention can also contain substances having therapeutic effectiveness. These substances can be for example hormones, antibiotics, or antimitotics.

In the compound according to the invention, the collagen fibers can advantageously be obtained starting from a material taken from the very subject who is to be treated by this compound.

EXAMPLE

In order to better understand the object of the invention, there now follows as a purely illustrative and non-limiting example a way of carrying out the invention.

In this example the preparation is described of a compound intended to be used as a dermal injection in skin breaks of a patient having wrinkles caused by old age.

During a first cosmetic-surgery operation, in particular a face lift or surgery to the breasts, thighs, or abdomen, a certain number of grams of skin are taken containing epidermis and 3 mm to 4 mm of adjacent skin. This skin of the subject has to start with been sterilized by the surgeon in the manner known in the art. Presuming a face lift, about 20 g of skin are obtained and one dissects this skin to eliminate any fat. One thus obtains about 10 g of starting material that has been stripped of fat that is sterile.

This material is comminuted immediately in an aqueous sterile solution of magnesium chloride buffered to a pH of 7.5 by a buffer (citric acid/tris). Three parts of saline solution are used for each part of skin. The comminution of the saline solution is done by means of a knife-type chopper for 30 min at 4° C. The suspension obtained is mixed for 12 h and maintained at 4° C. The mixture is then passed through a sieve having a mesh opening of 0.25 mm so as to separate it into a liquid phase and a solid residue. During this first extraction phase the saline solution has a concentration of 0.10M. The solid residue separated out is taken and subjected to a new extraction operation with a solution of magnesium chloride at 0.3M. The same extraction process is used again so as to be able to obtain a new liquid fraction. Again the solid residue is taken and one does five successive extractions, the concentration of magnesium chloride of the saline solution used being increased from extraction to extraction so as to attain a value of 1M at the last extraction. These five liquid fractions that are obtained are mixed and constitute the fibril suspension that will be subjected to the fibrillogenesis step.

The suspension of fibrils thus obtained is diluted by adding to it twenty time its volume of sterile water and one adds into this suspension while agitating it lightly N-acetyl neuraminic acid in order to obtain a concentration of 0.02M. The mixing is stop and the suspension is heated to 37° C. for 30min. Then the temperature is lowered to 4° C. and is maintained at this level for 16 h. A solid fraction forms slowly at the base of the vessel. The top fraction which contains the hydrosoluble protein fractions is removed. The solid residue is recovered on a sieve having a mesh size of 0.1 mm in order to separate the tissue residues. The filtrate is a suspension of collagen fibers. The suspension thus obtained is checked on an electron microscope. If protein elements are found to stick to the collagen fibers, the fibers are rinsed by means of a detergent. In order to do this one adds into the suspension of fibers 0.2% of sorbitan sol under the tradename "TWEEN 20" and the mixture is agitated for 12 hours. It is then decanted to extract the top fraction and rinsed with water, the decantation operation and the rinsing being done ten times in succession in order to assure the total extraction of the detergent. One checks again with the electronic microscope that the collagen fibers thus obtained are perfectly clean.

All of the above-described operations are carried out in conditions of surgical sterility without adding any antiseptic and without irradiation.

The obtained suspension is used to form an injectable compound containing 7% by volume of fibers in the presence of a sodium PBS buffer which adjusts the pH to a value of 7.3. This buffer corresponds to the following formula:

0.1M of monosodium phosphate,
0.1M of disodium phosphate, and
0.10M of sodium chloride.

This compound is held at 4° C. and is injected several days after its preparation into the skin breaks of the wrinkles of the subject from whom the skin serving as starting material has been taken. It is possible to confirm that the setting in place of the collagen fibers in the skin breaks allows one to obtain excellent results with no allergic reaction. The result is in addition long-term, which constitutes a considerable advantage relative to the prior use of bovine collagen whose effects disappeared at the end of several months.

I claim:

1. A method of obtaining human-skin collagen fibers from sterile pieces of human skin, the method comprising the steps of:
   a) comminuting the sterile skin such that it can pass through a sieve having a mesh size of 0.25 mm;
   b) mixing the comminuted sterile skin with a sterile aqueous solution of an alkaline-metal or alkaline-earth salt to form a suspension;
   c) diluting the suspension with a promoter of fibrillogenesis taken from the group formed by acetylated glucosamine, n-acetyl enuraminic acid, and mixtures thereof and setting the Ph of the suspension to a value between 4 and 6;
   d) maturating the diluted suspension at a temperature brought to between 30° C. and 50° C. in a time of less than two hours and then holding the diluted suspension at between 0° C. and 10° C. for a time between 10 hours and 50 hours such that collagen fibers grow in the suspension;
   e) separating collagen fibers from the suspension and checking them for the presence of protein impurities; and
   f) on discovering any protein impurities, rinsing the fibers by agitation with an atoxic aqueous solution of a nonionic detergent, then separating out substantially all of the residual protein impurities to obtain an aqueous suspension of collagen fibers having no foreign matter, and rinsing the collagen fibers in sterilized water.

2. The method defined in claim 1 wherein step b) uses an aqueous solution of a magnesium salt at a basic pH below 8.

3. The method defined in claim 2 wherein step b) is conducted in several generally identical substeps each of which produces a solid residue that is used in the following substep, the molar concentration of magnesium salt of the solution increasing progressively from 0.1 to 1M in passing from the first to the last substep.

4. The method defined claim 1 wherein step f) includes the substep of washing the fibers with a sorbitan solution.

5. The method defined in claim 4 wherein the sorbitan wash solution has a volume concentration of sorbitan equal to between 0.05% and 0.4%.

6. The method defined in claim 1 wherein the fibrilogenesis promoter is used at a concentration between 0.005M and 0.05M in the suspension after dilution.

7. The method defined in claim 1 wherein before adding the fibrillogenesis promoter the suspension is diluted from 10 to 30 times by addition of sterile water.

8. The method defined in claim 1 wherein in step e) the fibers are separated from the mother liquor by decanting the supernatant, the remaining part being recovered by straining out a decanted product containing the fibers.

9. Fibers obtained by the method of claim 1.

10. An injectable composition usable for treating the human body, the composition consisting of an aqueous suspension of fibers produced as defined in claim 17 in a volume concentration of between 1% and 15%.

11. The composition defined in claim 10 wherein the aqueous phase of the suspension is a phosphate buffer having a pH between 7 and 7.5.

12. The composition defined in claim 11 wherein the buffer contains 0.1M of monosodium phosphate, 0.1M of disodium phosphate, and 0.1M of sodium chloride and has a pH of about 7.3.

13. The composition defined in claim 10 wherein the collagen fibers are obtained from a starting material taken from the patient who is to be treated with the composition.

* * * * *